(12) United States Patent
Sartor

(10) Patent No.: US 7,834,484 B2
(45) Date of Patent: Nov. 16, 2010

(54) CONNECTION CABLE AND METHOD FOR ACTIVATING A VOLTAGE-CONTROLLED GENERATOR

(75) Inventor: Joe D. Sartor, Longmont, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 542 days.

(21) Appl. No.: 11/879,180

(22) Filed: Jul. 16, 2007

(65) Prior Publication Data

US 2009/0024120 A1    Jan. 22, 2009

(51) Int. Cl.
*A61B 18/00*    (2006.01)

(52) U.S. Cl. ............... 307/116; 307/147; 307/125; 307/130

(58) Field of Classification Search ............ 307/116, 307/125, 130, 147
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Isikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |

(Continued)

FOREIGN PATENT DOCUMENTS

DE    179607    3/1905

(Continued)

OTHER PUBLICATIONS

International Search Report EP 06010499.9 dated Jan. 29, 2008.

(Continued)

*Primary Examiner*—Fritz M Fleming

(57) ABSTRACT

A connection cable is disclosed for controlling a voltage-controlled generator such as an electrosurgery generator from a controlling device such as a robotic surgery system. The cable includes a first connector adapted to connect to a voltage-controlled generator and a second connector adapted to connect to a controlling device. Within the cable is a voltage divider interdisposed between the first connector and the second connector. The voltage divider is configured to divide a reference voltage provided by the voltage-controlled generator into at least one control voltage which is selectable by the controlling device. The cable additionally includes a plurality of electrical wires which operatively connect the first connector, the second connector and the voltage divider. During robotic electrosurgery, said operating parameters can be actuated by a surgeon operating at the robotic surgical system console, which causes a corresponding control voltage to be switched to a control voltage input on an electrosurgery generator, which, in turn, generates a corresponding electrosurgical signal in response thereto.

14 Claims, 5 Drawing Sheets

U.S. PATENT DOCUMENTS

| | | | |
|---|---|---|---|
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A * | 10/1973 | Podowski ................... 455/353 |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,110 A | 8/1974 | Colin |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A * | 8/1984 | Garito et al. ................... 606/42 |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |

| | | | | | |
|---|---|---|---|---|---|
| 4,907,589 A | 3/1990 | Cosman | 5,383,874 A | 1/1995 | Jackson |
| 4,922,210 A | 5/1990 | Flachenecker et al. | 5,383,876 A | 1/1995 | Nardella |
| 4,931,047 A | 6/1990 | Broadwin et al. | 5,383,917 A | 1/1995 | Desai et al. |
| 4,931,717 A | 6/1990 | Gray et al. | 5,385,148 A | 1/1995 | Lesh et al. |
| 4,938,761 A | 7/1990 | Ensslin | 5,400,267 A | 3/1995 | Denen et al. |
| 4,942,313 A | 7/1990 | Kinzel | 5,403,311 A | 4/1995 | Abele et al. |
| 4,959,606 A | 9/1990 | Forge | 5,403,312 A | 4/1995 | Yates et al. |
| 4,961,047 A | 10/1990 | Carder | 5,409,000 A | 4/1995 | Imran |
| 4,961,435 A | 10/1990 | Kitagawa et al. | 5,409,485 A | 4/1995 | Suda |
| 4,966,597 A | 10/1990 | Cosman | 5,413,573 A | 5/1995 | Koivukangas |
| 4,969,885 A | 11/1990 | Farin | 5,414,238 A | 5/1995 | Steigerwald et al. |
| 4,992,719 A | 2/1991 | Harvey | 5,417,719 A | 5/1995 | Hull et al. |
| 4,993,430 A | 2/1991 | Shimoyama et al. | 5,422,567 A | 6/1995 | Matsunaga |
| 4,995,877 A | 2/1991 | Ams et al. | 5,422,926 A | 6/1995 | Smith et al. |
| 5,015,227 A | 5/1991 | Broadwin et al. | 5,423,808 A | 6/1995 | Edwards et al. |
| 5,024,668 A | 6/1991 | Peters et al. | 5,423,809 A | 6/1995 | Klicek |
| 5,044,977 A | 9/1991 | Vindigni | 5,423,810 A | 6/1995 | Goble et al. |
| 5,067,953 A | 11/1991 | Feucht | 5,423,811 A | 6/1995 | Imran et al. |
| 5,075,839 A | 12/1991 | Fisher et al. | 5,425,704 A | 6/1995 | Sakurai et al. |
| 5,087,257 A | 2/1992 | Farin | 5,429,596 A | 7/1995 | Arias et al. |
| 5,099,840 A | 3/1992 | Goble et al. | 5,430,434 A | 7/1995 | Lederer et al. |
| 5,103,804 A | 4/1992 | Abele et al. | 5,432,459 A | 7/1995 | Thompson |
| 5,108,389 A | 4/1992 | Cosmescu | 5,433,739 A | 7/1995 | Sluijter et al. |
| 5,108,391 A | 4/1992 | Flachenecker | 5,436,566 A | 7/1995 | Thompson |
| 5,119,284 A | 6/1992 | Fisher et al. | 5,438,302 A | 8/1995 | Goble |
| 5,122,137 A | 6/1992 | Lennox | 5,443,463 A | 8/1995 | Stern et al. |
| 5,127,041 A | 6/1992 | O'Sullivan | 5,445,635 A | 8/1995 | Denen |
| 5,133,711 A | 7/1992 | Hagen | 5,451,224 A | 9/1995 | Goble et al. |
| 5,151,102 A | 9/1992 | Kamiyama et al. | 5,452,725 A | 9/1995 | Martenson |
| 5,152,762 A | 10/1992 | McElhenney | 5,454,809 A | 10/1995 | Janssen |
| 5,157,603 A | 10/1992 | Scheller et al. | 5,458,597 A | 10/1995 | Edwards et al. |
| 5,160,334 A | 11/1992 | Billings et al. | 5,462,521 A | 10/1995 | Brucker et al. |
| 5,161,893 A | 11/1992 | Shigezawa et al. | 5,472,441 A | 12/1995 | Edwards et al. |
| 5,167,658 A | 12/1992 | Ensslin | 5,472,443 A | 12/1995 | Cordis et al. |
| 5,167,659 A | 12/1992 | Ohtomo et al. | 5,474,464 A | 12/1995 | Drewnicki |
| 5,190,517 A | 3/1993 | Zieve et al. | 5,480,399 A | 1/1996 | Hebborn |
| 5,196,008 A | 3/1993 | Kuenecke | 5,483,952 A | 1/1996 | Aranyi |
| 5,196,009 A | 3/1993 | Kirwan, Jr. | 5,485,312 A | 1/1996 | Horner et al. |
| 5,201,900 A | 4/1993 | Nardella | 5,496,312 A | 3/1996 | Klicek |
| 5,207,691 A | 5/1993 | Nardella | 5,496,313 A | 3/1996 | Gentelia et al. |
| 5,230,623 A | 7/1993 | Guthrie et al. | 5,496,314 A | 3/1996 | Eggers |
| 5,233,515 A | 8/1993 | Cosman | 5,500,012 A | 3/1996 | Brucker et al. |
| 5,234,427 A | 8/1993 | Ohtomo et al. | 5,500,616 A | 3/1996 | Ochi |
| 5,249,121 A | 9/1993 | Baum et al. | 5,511,993 A | 4/1996 | Yamada et al. |
| 5,249,585 A | 10/1993 | Turner et al. | 5,514,129 A | 5/1996 | Smith |
| 5,254,117 A | 10/1993 | Rigby et al. | 5,520,684 A | 5/1996 | Imran |
| RE34,432 E | 11/1993 | Bertrand | 5,531,774 A | 7/1996 | Schulman et al. |
| 5,267,994 A | 12/1993 | Gentelia et al. | 5,534,018 A | 7/1996 | Wahlstrand et al. |
| 5,267,997 A | 12/1993 | Farin | 5,536,267 A | 7/1996 | Edwards et al. |
| 5,281,213 A | 1/1994 | Milder et al. | 5,540,677 A | 7/1996 | Sinofsky |
| 5,282,840 A | 2/1994 | Hudrlik | 5,540,681 A | 7/1996 | Strul et al. |
| 5,290,283 A | 3/1994 | Suda | 5,540,682 A | 7/1996 | Gardner et al. |
| 5,295,857 A | 3/1994 | Toly | 5,540,683 A | 7/1996 | Ichikawa |
| 5,300,068 A | 4/1994 | Rosar et al. | 5,540,684 A | 7/1996 | Hassler, Jr. |
| 5,300,070 A | 4/1994 | Gentelia | 5,541,376 A | 7/1996 | Ladtkow et al. |
| 5,304,917 A | 4/1994 | Somerville | 5,545,161 A | 8/1996 | Imran |
| 5,318,563 A | 6/1994 | Malis et al. | 5,556,396 A | 9/1996 | Cohen et al. |
| 5,323,778 A | 6/1994 | Kandarpa et al. | 5,558,671 A | 9/1996 | Yates |
| 5,324,283 A | 6/1994 | Heckele | 5,562,720 A | 10/1996 | Stern et al. |
| 5,330,518 A | 7/1994 | Neilson et al. | 5,569,242 A | 10/1996 | Lax et al. |
| 5,334,183 A | 8/1994 | Wuchinich | 5,571,147 A | 11/1996 | Sluijter et al. |
| 5,334,193 A | 8/1994 | Nardella | 5,573,533 A | 11/1996 | Strul |
| 5,341,807 A | 8/1994 | Nardella | 5,584,830 A | 12/1996 | Ladd et al. |
| 5,342,356 A * | 8/1994 | Ellman et al. ................. 606/32 | 5,588,432 A | 12/1996 | Crowley |
| 5,342,357 A | 8/1994 | Nardella | 5,596,466 A | 1/1997 | Ochi |
| 5,342,409 A | 8/1994 | Mullett | 5,599,344 A | 2/1997 | Paterson |
| 5,346,406 A | 9/1994 | Hoffman et al. | 5,599,345 A | 2/1997 | Edwards et al. |
| 5,346,491 A | 9/1994 | Oertli | 5,599,348 A | 2/1997 | Gentelia et al. |
| 5,348,554 A | 9/1994 | Imran et al. | 5,605,150 A | 2/1997 | Radons et al. |
| 5,370,645 A | 12/1994 | Klicek et al. | 5,609,560 A | 3/1997 | Ichikawa et al. |
| 5,370,672 A | 12/1994 | Fowler et al. | 5,613,966 A | 3/1997 | Makower et al. |
| 5,370,675 A | 12/1994 | Edwards et al. | 5,620,481 A | 4/1997 | Desai et al. |
| 5,372,596 A | 12/1994 | Klicek et al. | 5,626,575 A | 5/1997 | Crenner |

| | | | | | | |
|---|---|---|---|---|---|---|
| 5,628,745 | A | 5/1997 | Bek | 5,908,444 | A | 6/1999 | Azure |
| 5,628,771 | A | 5/1997 | Mizukawa et al. | 5,913,882 | A | 6/1999 | King |
| 5,643,330 | A | 7/1997 | Holsheimer et al. | 5,921,982 | A | 7/1999 | Lesh et al. |
| 5,647,869 | A | 7/1997 | Goble et al. | 5,925,070 | A | 7/1999 | King et al. |
| 5,647,871 | A | 7/1997 | Levine et al. | 5,931,836 | A | 8/1999 | Hatta et al. |
| 5,651,780 | A | 7/1997 | Jackson et al. | 5,938,690 | A | 8/1999 | Law et al. |
| 5,658,322 | A | 8/1997 | Fleming | 5,944,553 | A | 8/1999 | Yasui et al. |
| 5,660,567 | A | 8/1997 | Nierlich et al. | 5,948,007 | A | 9/1999 | Starkebaum et al. |
| 5,664,953 | A | 9/1997 | Reylek | 5,951,545 | A | 9/1999 | Schilling |
| 5,674,217 | A | 10/1997 | Wahlstrom et al. | 5,951,546 | A | 9/1999 | Lorentzen |
| 5,678,568 | A | 10/1997 | Uchikubo et al. | 5,954,686 | A | 9/1999 | Garito et al. |
| 5,681,307 | A | 10/1997 | McMahan | 5,954,717 | A | 9/1999 | Behl et al. |
| 5,685,840 | A | 11/1997 | Schechter et al. | 5,954,719 | A | 9/1999 | Chen et al. |
| 5,688,267 | A | 11/1997 | Panescu et al. | 5,957,961 | A | 9/1999 | Maguire et al. |
| 5,693,042 | A | 12/1997 | Bioarski et al. | 5,959,253 | A | 9/1999 | Shinchi |
| 5,693,078 | A | 12/1997 | Desai et al. | 5,961,344 | A | 10/1999 | Rosales et al. |
| 5,694,304 | A | 12/1997 | Telefus et al. | 5,964,746 | A * | 10/1999 | McCary ..................... 606/1 |
| 5,695,494 | A | 12/1997 | Becker | 5,971,980 | A | 10/1999 | Sherman |
| 5,696,441 | A | 12/1997 | Mak et al. | 5,971,981 | A | 10/1999 | Hill et al. |
| 5,697,925 | A | 12/1997 | Taylor | 5,976,128 | A | 11/1999 | Schilling et al. |
| 5,697,927 | A | 12/1997 | Imran et al. | 5,983,141 | A | 11/1999 | Sluijter et al. |
| 5,702,386 | A | 12/1997 | Stern et al. | 6,007,532 | A | 12/1999 | Netherly |
| 5,702,429 | A | 12/1997 | King | 6,010,499 | A | 1/2000 | Cobb |
| 5,707,369 | A | 1/1998 | Vaitekunas et al. | 6,013,074 | A | 1/2000 | Taylor |
| 5,712,772 | A | 1/1998 | Telefus et al. | 6,014,581 | A | 1/2000 | Whayne et al. |
| 5,713,896 | A | 2/1998 | Nardella | 6,017,338 | A | 1/2000 | Brucker et al. |
| 5,718,246 | A | 2/1998 | Vona | 6,022,346 | A | 2/2000 | Panescu et al. |
| 5,720,742 | A | 2/1998 | Zacharias | 6,022,347 | A | 2/2000 | Lindenmeier et al. |
| 5,720,744 | A | 2/1998 | Eggleston et al. | 6,033,399 | A | 3/2000 | Gines |
| 5,722,975 | A | 3/1998 | Edwards et al. | 6,039,731 | A | 3/2000 | Taylor et al. |
| 5,729,448 | A | 3/1998 | Haynie et al. | 6,039,732 | A | 3/2000 | Ichikawa et al. |
| 5,733,281 | A | 3/1998 | Nardella | 6,041,260 | A | 3/2000 | Stern et al. |
| 5,735,846 | A | 4/1998 | Panescu et al. | 6,044,283 | A | 3/2000 | Fein et al. |
| 5,738,683 | A | 4/1998 | Osypka | 6,053,910 | A | 4/2000 | Fleenor |
| 5,743,900 | A | 4/1998 | Hara | 6,053,912 | A | 4/2000 | Panescu et al. |
| 5,743,903 | A | 4/1998 | Stern et al. | 6,055,458 | A | 4/2000 | Cochran et al. |
| 5,749,869 | A | 5/1998 | Lindenmeier et al. | 6,056,745 | A | 5/2000 | Panescu et al. |
| 5,749,871 | A | 5/1998 | Hood et al. | 6,056,746 | A | 5/2000 | Goble et al. |
| 5,755,715 | A | 5/1998 | Stern | 6,059,781 | A | 5/2000 | Yamanashi et al. |
| 5,766,153 | A | 6/1998 | Eggers et al. | 6,063,075 | A | 5/2000 | Mihori |
| 5,766,165 | A | 6/1998 | Gentelia et al. | 6,063,078 | A | 5/2000 | Wittkampf |
| 5,769,847 | A | 6/1998 | Panescu | 6,066,137 | A | 5/2000 | Greep |
| 5,772,659 | A | 6/1998 | Becker et al. | 6,068,627 | A | 5/2000 | Orszulak et al. |
| 5,788,688 | A | 8/1998 | Bauer et al. | 6,074,089 | A | 6/2000 | Hollander et al. |
| 5,792,135 | A | 8/1998 | Madhani et al. | 6,074,386 | A | 6/2000 | Goble et al. |
| 5,792,138 | A | 8/1998 | Shipp | 6,074,388 | A | 6/2000 | Tockweiler et al. |
| 5,797,902 | A | 8/1998 | Netherly | 6,080,149 | A | 6/2000 | Huang et al. |
| 5,807,253 | A | 9/1998 | Dumoulin et al. | 6,088,614 | A | 7/2000 | Swanson |
| 5,810,804 | A | 9/1998 | Gough et al. | 6,093,186 | A | 7/2000 | Goble |
| 5,814,092 | A | 9/1998 | King | 6,102,497 | A | 8/2000 | Ehr et al. |
| 5,817,091 | A | 10/1998 | Nardella et al. | 6,102,907 | A | 8/2000 | Smethers et al. |
| 5,817,093 | A | 10/1998 | Williamson, IV et al. | 6,113,591 | A | 9/2000 | Whayne et al. |
| 5,820,568 | A | 10/1998 | Willis | 6,113,592 | A | 9/2000 | Taylor |
| 5,827,271 | A | 10/1998 | Buysse et al. | 6,113,593 | A | 9/2000 | Tu et al. |
| 5,830,212 | A | 11/1998 | Cartmell | 6,113,596 | A | 9/2000 | Hooven |
| 5,836,909 | A | 11/1998 | Cosmescu | 6,123,701 | A | 9/2000 | Nezhat |
| 5,836,943 | A | 11/1998 | Miller, III | 6,123,702 | A | 9/2000 | Swanson et al. |
| 5,836,990 | A | 11/1998 | Li | 6,132,429 | A | 10/2000 | Baker |
| 5,843,019 | A | 12/1998 | Eggers et al. | 6,142,992 | A | 11/2000 | Cheng et al. |
| 5,843,075 | A | 12/1998 | Taylor | 6,155,975 | A | 12/2000 | Urich et al. |
| 5,846,236 | A | 12/1998 | Lindenmeier et al. | 6,162,184 | A | 12/2000 | Swanson et al. |
| 5,849,010 | A | 12/1998 | Wurzer et al. | 6,162,217 | A | 12/2000 | Kannenberg et al. |
| 5,853,409 | A | 12/1998 | Swanson et al. | 6,165,169 | A | 12/2000 | Panescu et al. |
| 5,860,832 | A | 1/1999 | Wayt et al. | 6,171,304 | B1 | 1/2001 | Netherly et al. |
| 5,865,788 | A | 2/1999 | Edwards et al. | 6,183,468 | B1 | 2/2001 | Swanson et al. |
| 5,868,737 | A | 2/1999 | Taylor et al. | 6,186,147 | B1 | 2/2001 | Cobb |
| 5,868,739 | A | 2/1999 | Lindenmeier et al. | 6,188,211 | B1 | 2/2001 | Rincon-Mora et al. |
| 5,868,740 | A | 2/1999 | LeVeen et al. | 6,193,713 | B1 | 2/2001 | Geistert et al. |
| 5,871,481 | A | 2/1999 | Kannenberg et al. | 6,197,023 | B1 | 3/2001 | Muntermann |
| 5,878,193 | A | 3/1999 | Wang et al. | 6,203,541 | B1 | 3/2001 | Keppel |
| 5,891,142 | A | 4/1999 | Eggers et al. | 6,210,403 | B1 | 4/2001 | Klicek |
| 5,897,552 | A | 4/1999 | Edwards et al. | 6,216,704 | B1 | 4/2001 | Ingle et al. |
| 5,906,614 | A | 5/1999 | Stern et al. | 6,222,356 | B1 | 4/2001 | Taghizadeh-Kaschani |

| | | | |
|---|---|---|---|
| 6,228,078 B1 | 5/2001 | Eggers et al. | |
| 6,228,080 B1 | 5/2001 | Gines | |
| 6,228,081 B1 | 5/2001 | Goble | |
| 6,231,569 B1 | 5/2001 | Bek | |
| 6,232,556 B1 | 5/2001 | Daugherty et al. | |
| 6,235,020 B1 | 5/2001 | Cheng et al. | |
| 6,235,022 B1 | 5/2001 | Hallock et al. | |
| 6,237,604 B1 | 5/2001 | Burnside et al. | |
| 6,238,387 B1 | 5/2001 | Miller, III | |
| 6,238,388 B1 | 5/2001 | Ellman | |
| 6,241,723 B1 | 6/2001 | Heim et al. | |
| 6,241,725 B1 | 6/2001 | Cosman | |
| 6,243,654 B1 | 6/2001 | Johnson et al. | |
| 6,245,061 B1 | 6/2001 | Panescu et al. | |
| 6,245,063 B1 | 6/2001 | Uphoff | |
| 6,245,065 B1 | 6/2001 | Panescu | |
| 6,246,912 B1 | 6/2001 | Sluijter et al. | |
| 6,251,106 B1 | 6/2001 | Becker et al. | |
| 6,254,422 B1 | 7/2001 | Feye-Hohmann | |
| 6,258,085 B1 | 7/2001 | Eggleston | |
| 6,261,285 B1 | 7/2001 | Novak | |
| 6,261,286 B1 | 7/2001 | Goble et al. | |
| 6,267,760 B1 | 7/2001 | Swanson | |
| 6,273,886 B1 | 8/2001 | Edwards | |
| 6,275,786 B1 | 8/2001 | Daners | |
| 6,293,941 B1 | 9/2001 | Strul | |
| 6,293,942 B1 | 9/2001 | Goble et al. | |
| 6,293,943 B1 | 9/2001 | Panescu et al. | |
| 6,296,636 B1 | 10/2001 | Cheng et al. | |
| 6,306,131 B1 | 10/2001 | Hareyama et al. | |
| 6,306,134 B1 | 10/2001 | Goble et al. | |
| 6,309,386 B1 | 10/2001 | Bek | |
| 6,322,558 B1 | 11/2001 | Taylor et al. | |
| 6,325,799 B1 | 12/2001 | Goble | |
| 6,331,181 B1 | 12/2001 | Tierney et al. | |
| 6,337,998 B1 | 1/2002 | Behl et al. | |
| 6,338,657 B1 | 1/2002 | Harper et al. | |
| 6,350,262 B1 | 2/2002 | Ashley | |
| 6,358,245 B1 | 3/2002 | Edwards | |
| 6,364,877 B1 | 4/2002 | Goble et al. | |
| 6,371,963 B1 | 4/2002 | Nishtala et al. | |
| 6,383,183 B1 | 5/2002 | Sekino et al. | |
| 6,391,024 B1 | 5/2002 | Sun et al. | |
| 6,398,779 B1 | 6/2002 | Buysse et al. | |
| 6,398,781 B1 | 6/2002 | Goble et al. | |
| 6,402,741 B1 | 6/2002 | Keppel et al. | |
| 6,402,742 B1 | 6/2002 | Blewett et al. | |
| 6,402,743 B1 | 6/2002 | Orszulak et al. | |
| 6,402,748 B1 | 6/2002 | Schoenman et al. | |
| 6,409,722 B1 | 6/2002 | Hoey et al. | |
| 6,413,256 B1 | 7/2002 | Truckai et al. | |
| 6,416,509 B1 | 7/2002 | Goble et al. | |
| 6,422,896 B2 | 7/2002 | Aoki et al. | |
| 6,423,057 B1 | 7/2002 | He et al. | |
| 6,426,886 B1 | 7/2002 | Goder | |
| 6,428,537 B1 | 8/2002 | Swanson et al. | |
| 6,436,096 B1 | 8/2002 | Hareyama | |
| 6,440,157 B1 | 8/2002 | Shigezawa et al. | |
| 6,451,015 B1 | 9/2002 | Rittman, III et al. | |
| 6,454,594 B2 | 9/2002 | Sawayanagi | |
| 6,458,121 B1 | 10/2002 | Rosenstock | |
| 6,458,122 B1 | 10/2002 | Pozzato | |
| 6,464,689 B1 | 10/2002 | Qin | |
| 6,464,696 B1 | 10/2002 | Oyama | |
| 6,468,270 B1 | 10/2002 | Hovda et al. | |
| 6,468,273 B1 | 10/2002 | Leveen et al. | |
| 6,482,201 B1 | 11/2002 | Olsen et al. | |
| 6,488,678 B2 | 12/2002 | Sherman | |
| 6,494,880 B1 | 12/2002 | Swanson et al. | |
| 6,497,659 B1 | 12/2002 | Rafert | |
| 6,498,466 B1 | 12/2002 | Edwards | |
| 6,506,189 B1 | 1/2003 | Rittman, III et al. | |
| 6,508,815 B1 | 1/2003 | Strul | |
| 6,511,476 B2 | 1/2003 | Hareyama | |
| 6,511,478 B1 | 1/2003 | Burnside | |
| 6,517,538 B1 | 2/2003 | Jacob et al. | |
| 6,522,931 B2 | 2/2003 | Manker et al. | |
| 6,524,308 B1 | 2/2003 | Muller et al. | |
| 6,537,272 B2 | 3/2003 | Christopherson et al. | |
| 6,544,260 B1 | 4/2003 | Markel et al. | |
| 6,546,270 B1 | 4/2003 | Goldin et al. | |
| 6,547,786 B1 | 4/2003 | Goble | |
| 6,557,559 B1 | 5/2003 | Eggers et al. | |
| 6,558,376 B2 | 5/2003 | Bishop | |
| 6,558,377 B2 | 5/2003 | Lee et al. | |
| 6,560,470 B1 | 5/2003 | Pologe | |
| 6,562,037 B2 | 5/2003 | Paton | |
| 6,565,559 B2 | 5/2003 | Eggleston | |
| 6,565,562 B1 | 5/2003 | Shah et al. | |
| 6,575,969 B1 | 6/2003 | Rittman, III et al. | |
| 6,578,579 B2 | 6/2003 | Burnside et al. | |
| 6,579,288 B1 | 6/2003 | Swanson et al. | |
| 6,582,427 B1 | 6/2003 | Goble et al. | |
| 6,602,243 B2 | 8/2003 | Noda | |
| 6,602,252 B2 | 8/2003 | Mollenauer | |
| 6,611,793 B1 | 8/2003 | Burnside et al. | |
| 6,620,157 B1 | 9/2003 | Dabney et al. | |
| 6,620,189 B1 | 9/2003 | Machold et al. | |
| 6,623,423 B2 | 9/2003 | Sakurai et al. | |
| 6,626,901 B1 | 9/2003 | Treat et al. | |
| 6,629,973 B1 | 10/2003 | Wardell et al. | |
| 6,632,193 B1 | 10/2003 | Davison et al. | |
| 6,635,056 B2 | 10/2003 | Kadhiresan et al. | |
| 6,635,057 B2 | 10/2003 | Harano | |
| 6,645,198 B1 | 11/2003 | Bommannan et al. | |
| 6,648,883 B2 | 11/2003 | Francischelli | |
| 6,651,669 B1 | 11/2003 | Burnside | |
| 6,652,513 B2 | 11/2003 | Panescu et al. | |
| 6,652,514 B2 * | 11/2003 | Ellman et al. | 606/37 |
| 6,653,569 B1 | 11/2003 | Sung | |
| 6,656,177 B2 | 12/2003 | Truckai et al. | |
| 6,663,623 B1 | 12/2003 | Oyama et al. | |
| 6,663,624 B2 | 12/2003 | Edwards | |
| 6,663,627 B2 | 12/2003 | Francischelli et al. | |
| 6,666,860 B1 | 12/2003 | Takahashi | |
| 6,672,151 B1 | 1/2004 | Schultz et al. | |
| 6,679,875 B2 | 1/2004 | Honda | |
| 6,682,527 B2 | 1/2004 | Strul | |
| 6,685,700 B2 | 2/2004 | Behl | |
| 6,685,701 B2 | 2/2004 | Orszulak et al. | |
| 6,685,703 B2 | 2/2004 | Pearson et al. | |
| 6,689,131 B2 | 2/2004 | McClurken | |
| 6,692,489 B1 | 2/2004 | Heim | |
| 6,693,782 B1 | 2/2004 | Lash | |
| 6,695,837 B2 | 2/2004 | Howell | |
| 6,696,844 B2 | 2/2004 | Wong et al. | |
| 6,712,813 B2 | 3/2004 | Ellman | |
| 6,730,078 B2 | 5/2004 | Simpson et al. | |
| 6,730,079 B2 | 5/2004 | Lovewell | |
| 6,730,080 B2 | 5/2004 | Harano | |
| 6,733,495 B1 | 5/2004 | Bek | |
| 6,733,498 B2 | 5/2004 | Paton | |
| 6,740,079 B1 | 5/2004 | Eggers | |
| 6,740,085 B2 | 5/2004 | Hareyama | |
| 6,743,225 B2 | 6/2004 | Sanchez et al. | |
| 6,746,284 B1 | 6/2004 | Spink, Jr. | |
| 6,749,624 B2 | 6/2004 | Knowlton | |
| 6,755,825 B2 | 6/2004 | Shoenman et al. | |
| 6,758,846 B2 | 7/2004 | Goble et al. | |
| 6,761,716 B2 | 7/2004 | Kadhiresan et al. | |
| 6,783,523 B2 | 8/2004 | Qin | |
| 6,784,405 B2 | 8/2004 | Flugstad et al. | |
| 6,786,905 B2 | 9/2004 | Swanson et al. | |
| 6,790,206 B2 | 9/2004 | Panescu | |
| 6,792,390 B1 | 9/2004 | Burnside et al. | |
| 6,796,980 B2 | 9/2004 | Hall | |

| | | | | | | |
|---|---|---|---|---|---|---|
| 6,796,981 B2 | 9/2004 | Wham | | 7,175,618 B2 | 2/2007 | Dabney et al. |
| 6,809,508 B2 | 10/2004 | Donofrio | | 7,175,621 B2 | 2/2007 | Heim et al. |
| 6,818,000 B2 | 11/2004 | Muller et al. | | 7,192,427 B2 | 3/2007 | Chapelon et al. |
| 6,824,539 B2 | 11/2004 | Novak | | 7,195,627 B2 | 3/2007 | Amoah et al. |
| 6,830,569 B2 | 12/2004 | Thompson | | 7,203,556 B2 | 4/2007 | Daners |
| 6,837,888 B2 | 1/2005 | Ciarrocca et al. | | 7,211,081 B2 | 5/2007 | Goble |
| 6,843,682 B2 | 1/2005 | Matsuda et al. | | 7,214,224 B2 | 5/2007 | Goble |
| 6,843,789 B2 | 1/2005 | Goble | | 7,217,269 B2 | 5/2007 | El-Galley et al. |
| 6,849,073 B2 | 2/2005 | Hoey | | 7,220,260 B2 | 5/2007 | Fleming et al. |
| 6,855,141 B2 | 2/2005 | Lovewell | | 7,223,264 B2 | 5/2007 | Daniel et al. |
| 6,855,142 B2 | 2/2005 | Harano | | 7,226,447 B2 | 6/2007 | Uchida et al. |
| 6,860,881 B2 | 3/2005 | Sturm | | 7,229,469 B1 | 6/2007 | Witzel et al. |
| 6,864,686 B2 | 3/2005 | Novak | | 7,232,437 B2 | 6/2007 | Berman et al. |
| 6,875,210 B2 | 4/2005 | Refior | | 7,238,181 B2 | 7/2007 | Daners et al. |
| 6,890,331 B2 | 5/2005 | Kristensen | | 7,238,183 B2 | 7/2007 | Kreindel |
| 6,893,435 B2 | 5/2005 | Goble | | 7,244,255 B2 | 7/2007 | Daners et al. |
| 6,899,538 B2 | 5/2005 | Matoba | | 7,247,155 B2 | 7/2007 | Hoey et al. |
| 6,923,804 B2 | 8/2005 | Eggers et al. | | 7,250,048 B2 | 7/2007 | Francischelli et al. |
| 6,929,641 B2 | 8/2005 | Goble et al. | | 7,250,746 B2 | 7/2007 | Oswald et al. |
| 6,936,047 B2 | 8/2005 | Nasab et al. | | 7,255,694 B2 | 8/2007 | Keppel |
| 6,939,344 B2 | 9/2005 | Kreindel | | 7,258,688 B1 | 8/2007 | Shah et al. |
| 6,939,346 B2 | 9/2005 | Kannenberg et al. | | 7,282,048 B2 | 10/2007 | Goble et al. |
| 6,939,347 B2 | 9/2005 | Thompson | | 7,282,049 B2 | 10/2007 | Orszulak et al. |
| 6,942,660 B2 | 9/2005 | Pantera et al. | | 7,285,117 B2 | 10/2007 | Krueger et al. |
| 6,948,503 B2 | 9/2005 | Refior et al. | | 7,294,127 B2 | 11/2007 | Leung et al. |
| 6,958,064 B2 | 10/2005 | Rioux et al. | | 7,300,435 B2 | 11/2007 | Wham et al. |
| 6,962,587 B2 | 11/2005 | Johnson et al. | | 7,300,437 B2 | 11/2007 | Pozzato |
| 6,966,907 B2 | 11/2005 | Goble | | 7,303,557 B2 | 12/2007 | Wham et al. |
| 6,970,752 B1 * | 11/2005 | Lim et al. ............... 700/94 | | 7,305,311 B2 | 12/2007 | Van Zyl |
| 6,974,453 B2 | 12/2005 | Woloszko et al. | | 7,317,954 B2 | 1/2008 | McGreevy |
| 6,974,463 B2 | 12/2005 | Magers et al. | | 7,317,955 B2 | 1/2008 | McGreevy |
| 6,977,495 B2 | 12/2005 | Donofrio | | 7,324,357 B2 | 1/2008 | Miura et al. |
| 6,984,231 B2 | 1/2006 | Goble | | 7,333,859 B2 | 2/2008 | Rinaldi et al. |
| 6,989,010 B2 | 1/2006 | Francischelli et al. | | 7,341,586 B2 | 3/2008 | Daniel et al. |
| 6,994,704 B2 | 2/2006 | Qin et al. | | 7,344,532 B2 | 3/2008 | Goble et al. |
| 6,994,707 B2 | 2/2006 | Ellman et al. | | 7,353,068 B2 | 4/2008 | Tanaka et al. |
| 7,001,379 B2 | 2/2006 | Behl et al. | | 7,354,436 B2 | 4/2008 | Rioux et al. |
| 7,001,381 B2 | 2/2006 | Harano et al. | | 7,357,800 B2 | 4/2008 | Swanson |
| 7,004,174 B2 | 2/2006 | Eggers et al. | | 7,364,577 B2 | 4/2008 | Wham et al. |
| 7,008,369 B2 | 3/2006 | Cuppen | | 7,364,578 B2 | 4/2008 | Francischelli et al. |
| 7,008,417 B2 | 3/2006 | Eick | | 7,364,972 B2 | 4/2008 | Ono et al. |
| 7,008,421 B2 | 3/2006 | Daniel et al. | | 7,367,972 B2 | 5/2008 | Francischelli et al. |
| 7,025,764 B2 | 4/2006 | Paton et al. | | RE40,388 E | 6/2008 | Gines |
| 7,033,351 B2 * | 4/2006 | Howell ............... 606/29 | | 7,396,336 B2 | 7/2008 | Orszulak et al. |
| 7,041,096 B2 | 5/2006 | Malis et al. | | 7,402,754 B2 | 7/2008 | Kirwan, Jr. et al. |
| 7,044,948 B2 | 5/2006 | Keppel | | D574,323 S | 8/2008 | Waaler |
| 7,044,949 B2 | 5/2006 | Orszulak et al. | | 7,407,502 B2 | 8/2008 | Strul et al. |
| 7,060,063 B2 | 6/2006 | Marion et al. | | 7,416,437 B2 | 8/2008 | Sartor et al. |
| 7,062,331 B2 | 6/2006 | Zarinetchi et al. | | 7,416,549 B2 | 8/2008 | Young et al. |
| 7,063,692 B2 | 6/2006 | Sakurai et al. | | 7,422,582 B2 | 9/2008 | Malackowski et al. |
| 7,066,933 B2 | 6/2006 | Hagg | | 7,422,586 B2 | 9/2008 | Morris et al. |
| 7,074,217 B2 | 7/2006 | Strul et al. | | 7,425,835 B2 | 9/2008 | Eisele |
| 7,083,618 B2 | 8/2006 | Couture et al. | | 7,465,302 B2 | 12/2008 | Odell et al. |
| 7,094,231 B1 | 8/2006 | Ellman et al. | | 7,470,272 B2 | 12/2008 | Mulier et al. |
| RE39,358 E | 10/2006 | Goble | | 7,479,140 B2 | 1/2009 | Ellman et al. |
| 7,115,121 B2 | 10/2006 | Novak | | 7,491,199 B2 | 2/2009 | Goble |
| 7,115,124 B1 | 10/2006 | Xiao | | 7,491,201 B2 | 2/2009 | Shields et al. |
| 7,118,564 B1 | 10/2006 | Ritchie et al. | | 7,513,896 B2 | 4/2009 | Orszulak |
| 7,122,031 B2 | 10/2006 | Edwards et al. | | 7,525,398 B2 | 4/2009 | Nishimura et al. |
| 7,131,445 B2 | 11/2006 | Amoah | | 2001/0014804 A1 | 8/2001 | Goble et al. |
| 7,131,860 B2 | 11/2006 | Sartor et al. | | 2001/0029315 A1 | 10/2001 | Sakurai et al. |
| 7,137,980 B2 | 11/2006 | Buysse et al. | | 2001/0031962 A1 | 10/2001 | Eggleston |
| 7,146,210 B2 | 12/2006 | Palti | | 2002/0035363 A1 | 3/2002 | Edwards et al. |
| 7,147,638 B2 | 12/2006 | Chapman et al. | | 2002/0035364 A1 | 3/2002 | Schoenman et al. |
| 7,151,964 B2 | 12/2006 | Desai et al. | | 2002/0052599 A1 | 5/2002 | Goble |
| 7,153,300 B2 | 12/2006 | Goble | | 2002/0068932 A1 | 6/2002 | Edwards |
| 7,156,842 B2 | 1/2007 | Sartor et al. | | 2002/0107517 A1 | 8/2002 | Witt et al. |
| 7,156,844 B2 | 1/2007 | Reschke et al. | | 2002/0111624 A1 | 8/2002 | Witt et al. |
| 7,156,846 B2 | 1/2007 | Dycus et al. | | 2002/0151889 A1 | 10/2002 | Swanson et al. |
| 7,160,293 B2 | 1/2007 | Sturm et al. | | 2002/0193787 A1 | 12/2002 | Qin |
| 7,163,536 B2 | 1/2007 | Godara | | 2003/0004510 A1 | 1/2003 | Wham et al. |
| 7,169,144 B2 | 1/2007 | Hoey et al. | | 2003/0060818 A1 | 3/2003 | Kannenberg |
| 7,172,591 B2 | 2/2007 | Harano et al. | | 2003/0078572 A1 | 4/2003 | Pearson et al. |

| | | |
|---|---|---|
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Flemming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0004634 A1 | 1/2005 | Ricart et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0109111 A1 | 5/2005 | Manlove et al. |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0184701 A1* | 8/2005 | Kendall ...................... 320/104 |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |

| | | |
|---|---|---|
| EP | 1707144 | 3/2006 |
| EP | 1645235 | 4/2006 |
| EP | 880220 | 6/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/39914 | 12/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2005/060365 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060849 | 7/2005 |
| WO | WO2006/050888 | 5/2006 |
| WO | WO2006/105121 | 10/2006 |

OTHER PUBLICATIONS

International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation—'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Muller et al. "Extended Left Hemicolectomy Using the LigaSure Vessel Sealing System" Innovations That Work; Sep. 1999.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.

International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07010673.7 dated Sep. 24, 2007.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
US 6,878,148, 04/2005, Goble et al. (withdrawn)

* cited by examiner

CONNECTION CABLE AND METHOD FOR ACTIVATING A VOLTAGE-CONTROLLED GENERATOR

BACKGROUND

1. Technical Field

The present disclosure relates generally to the field of minimally invasive surgery performed using electrosurgical techniques, and in particular, to a connection cable and method for connecting an electrosurgery generator to a robotic surgery system, enabling the electrosurgical generator to be controlled by a surgeon at the robotic master console.

2. Background of Related Art

Electrosurgery is a technique of using alternating current electrical signals, using a carrier frequency in the approximately 200 kHz-3.3 mHz range, in connection with surgical instruments, to cut or coagulate biologic tissue endogenically. This electrosurgical signal can be a sinusoidal waveform operating in a continuous mode at a 100% duty cycle, or pulse modulated at a duty cycle of less than 100%. Typically, electrosurgical signals are operated at 100% duty cycle for maximal cutting effect, and are pulse modulated at duty cycles ranging from 50% to 25% for less aggressive cutting, also referred to as blending, or, at a substantially lower duty cycle of approximately 6%, for coagulating. The electrosurgical carrier signal can also be varied in intensity. The electrosurgical signal is applied to the patient via electrodes in either monopolar mode, or bipolar mode. In monopolar mode, the active electrode is the surgical instrument at the surgical site, and the return electrode is elsewhere on the patient, such that the electrosurgical signal passes through the patient's body from the surgical site to the return electrode. In bipolar mode, both the active and return electrodes are at the surgical site, effectuated by, for example, both tines of a pair of forceps, such that the electrosurgical signal passes through only the tissue that is held between the tines of the instrument. A surgeon's decision to use monopolar or bipolar mode electrosurgery is often based upon various factors, including for example the type of procedure to be performed, or whether the patient is fitted with a metallic prosthesis or cardiac pacemaker.

A surgeon performs robotic surgery by sitting at a robotic master console and viewing a three-dimensional virtual operative field, while manipulating controls that remotely control robotic arms mounted on a separate robotic surgical cart. The robotic arms hold surgical instruments that follow the surgeon's hand motions, and a stereoscopic video camera that transmits a three-dimensional view of the operative field to the surgeon. The three-dimensional imaging, the hand-like motions of the robotic instruments, and the ability to assist the surgeon through motion scaling and tremor reduction techniques facilitate advanced minimally-invasive procedures that could not otherwise be performed using traditional endoscopic techniques.

When performing electrosurgery with manual (non-robotic) instruments, a surgeon can actuate an electrosurgery generator using hand switches located on the surgical instrument. For example, the surgeon can selectively apply a cutting waveform, a blending waveform or a coagulating waveform using the hand controls. However, this is not desirable or practical in the case of robotic surgery, because the surgical instruments are remotely controlled by a surgeon who is operating a robotic master console, which is located away from the patient.

The use of existing electrosurgery generators with robotic surgery systems without the need to modify or upgrade existing electrosurgery generators would be a great achievement in electrosurgery and may ultimately achieve interoperability with robotic surgery systems and minimize or eliminate training and certification requirements imposed on physicians and other medical facility staff arising from the deployment of such modified electrosurgery generators.

SUMMARY

It is an aspect of the present disclosure to provide a connection cable for actuating a voltage-controlled generator from a controlling device. Control signals originating within a controlling device are adapted for use by the voltage-controlled generator by an interface provided within the cable. In an embodiment, the cable has a first end, which includes a first connector adapted to connect to a voltage-controlled generator, such as an electrosurgery generator; a second end, which includes a second connector adapted to connect to a controlling device, such as a remotely-controlled robotic surgery system. A voltage divider is interdisposed between the first connector and the second connector, the voltage divider being configured to divide a reference voltage provided by the electrosurgery generator into at least one control voltage for selection by the controlling device. Each control voltage corresponds to an operating mode, command or parameter related to the electrosurgery generator, for example, a cut operation, a blend operation, and a coagulate operation. The connection cable includes a plurality of electrical conductors which operatively connect the first connector, the second connector, and the voltage divider.

Control signals in the form of at least one switch closure, each corresponding to a desired operating mode of the electrosurgery generator, originate within the robotic surgery system. The switch closure completes an electrical circuit whereby a corresponding control voltage is routed from the voltage divider to a mode input of the electrosurgery generator, which, in turn, generates the desired electrosurgery signal.

In an embodiment of the present disclosure, the voltage dividing network is disposed between +5 volts dc (+5Vdc) and ground (0Vdc) and is configured to provide at least one control voltage corresponding to an operating mode of the electrosurgery generator. In an embodiment, the voltage divider is comprised of four resistors connected in series, which, continuing with the present example, provides, in addition to the reference voltages of 0Vdc and +5.0Vdc, three voltage taps, making available at each tap a control voltage corresponding to an operating mode of the electrosurgical generator, for example, a cutting, blending and coagulating mode. Each voltage tap is operably connected to a first contact of a switch configured for switching the voltage tap to the mode input of an electrosurgery generator.

In an embodiment, the switch includes a normally-open single pole single throw (SPST) switch within the robotic master console for actuation by a surgeon. It is also envisioned that the at least one switch can be a set of relay contacts, a solid-state switch, or inductive, capacitive, or other switching means as now or in the future may be known, capable of actuation by a surgeon operating the robotic surgery console and/or by the operational software of the robotic surgery system. A contact of each SPST switch is commonly and operably connected to a control input, also known as a mode input, of the electrosurgery generator configured to sense the presence of a control voltage and to produce a corresponding electrosurgical signal in response thereto. When the at least one SPST switch is closed, an electrical circuit is completed whereby a control voltage is applied to the mode input of an electrosurgery generator, which causes a corresponding electrosurgical signal to be produced in accordance with the present disclosure.

In addition to control signals disclosed herein, the present disclosure contemplates that the generated electrosurgery signal be transmitted from the electrosurgery generator to the surgical instrument, or to the robotic surgery system, by a transmission wire within the connection cable herein described.

Also envisioned is a connection cable capable of interfacing a plurality of electrosurgery generators to a single controlling device, such as a robotic surgery system. Such plurality of electrosurgery generators can be of a type which are collectively housed in a single chassis or operating unit, or housed separately in individual chassis. Such plurality of electrosurgery generators can share a common control port whereby a single connection from the robotic surgical system is capable of controlling said plurality of electrosurgery generators.

The present disclosure further provides for a connection cable adapted for use with an existing hand switch interface port on an electrosurgery generator. The hand switch interface port is typically situated on the front panel of an electrosurgery generator thereby enabling the switch interface to be used with a robotic surgery system without requiring hardware or software modifications to known electrosurgery generators which are in popular use.

A method for interfacing an electrosurgery generator to a robotic surgery system is also disclosed wherein at least one control signal originating within a robotic surgery system is adapted for use by the electrosurgery generator by an interface provided within the cable. The method further includes the steps of: providing a voltage-controlled electrosurgery generator and a robotic surgery system electrically coupled thereto; dividing a reference voltage provided by the voltage-controlled generator into at least one control voltage; interfacing control signals originating within the robotic surgery system or other controlling system to the electrosurgery generator via a connector adapted for connecting to the robotic surgery system; selecting an at least one control voltage in accordance with a control signal originating within the robotic surgery system; and applying the control voltage to a control input of an electrosurgery generator adapted to sense the presence of said control voltage and to produce a corresponding electrosurgical signal in response thereto.

It is envisioned that the steps of the method in accordance with the present disclosure can be performed in a different ordering than the ordering provided herein.

The present disclosure further contemplates an apparatus for performing robotic electrosurgery comprising an electrosurgery generator configured to accept a control voltage at a control voltage input and to produce a corresponding electrosurgical signal in response thereto. A surgeon, from the robotic master console, can cause to be activated a control signal corresponding to an electrosurgery signal. An interface may be configured to convert the control signal into a control voltage and to apply the control voltage to the control voltage input of the electrosurgery generator, thereby causing an electrosurgery signal to be generated. In an embodiment, the interface includes a voltage divider for providing at least one control voltage for application to the control voltage input of the electrosurgery generator via at least one switch. Optionally, the interface is additionally configured to transmit the electrosurgical signal to a surgical instrument of the robotic surgical system.

BRIEF DESCRIPTION OF THE DRAWINGS

Various embodiments of the present disclosure will be described herein below with reference to the figures wherein.

DETAILED DESCRIPTION

Figure 1A:
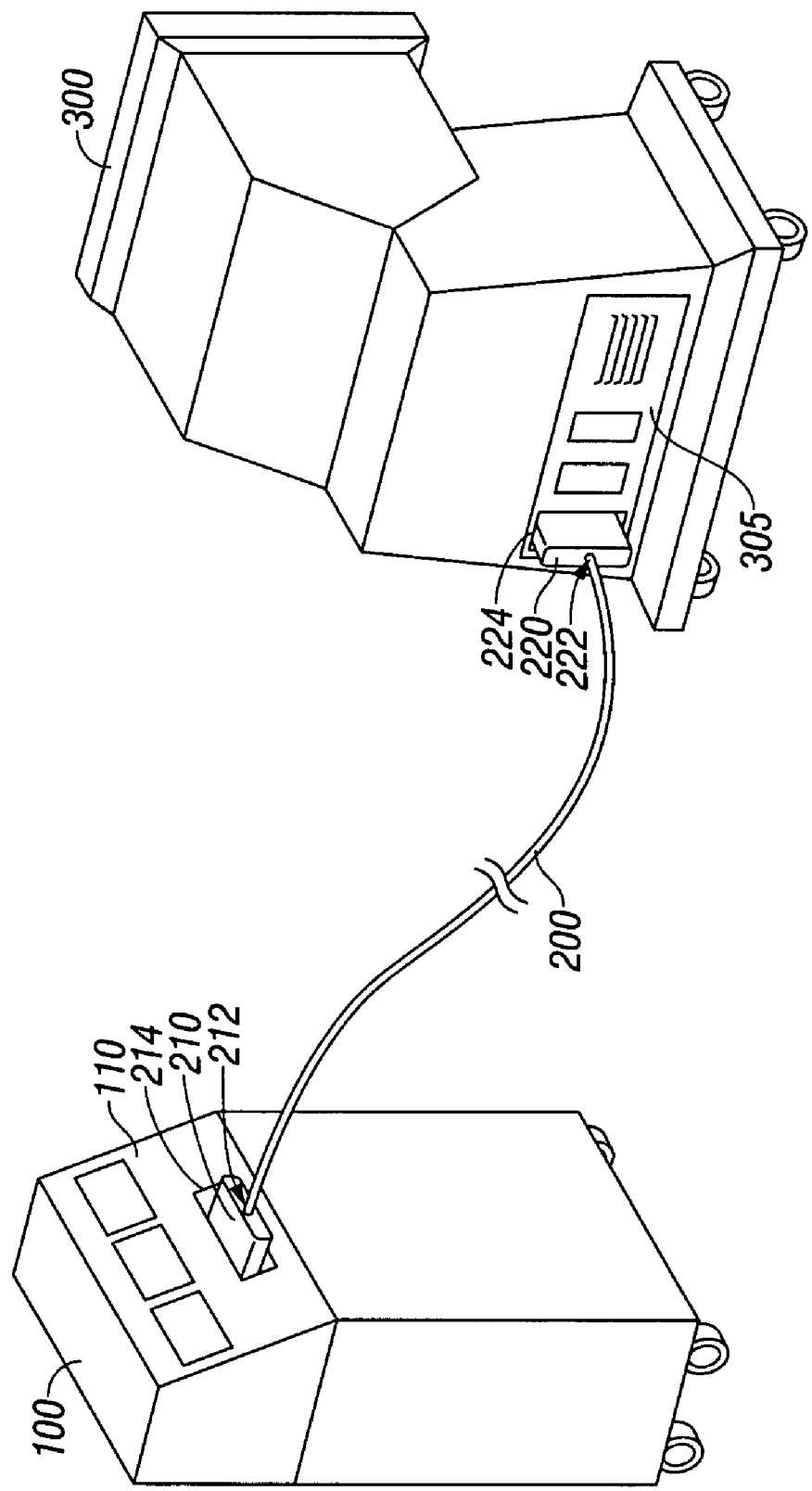
FIG. 1A is a schematic of an electrosurgery generator coupled to a robotic surgery system master console according to an embodiment of the present disclosure.

Embodiments of the presently disclosed connection cable are described herein in detail with reference to the drawings, in which like reference numerals designate identical or corresponding elements in each of the several views.

The present disclosure provides a connection cable for connecting an electrosurgery generator to a robotic surgical system enabling the electrosurgical generator to be controlled by a surgeon at the robotic master console.

Figure 1B:
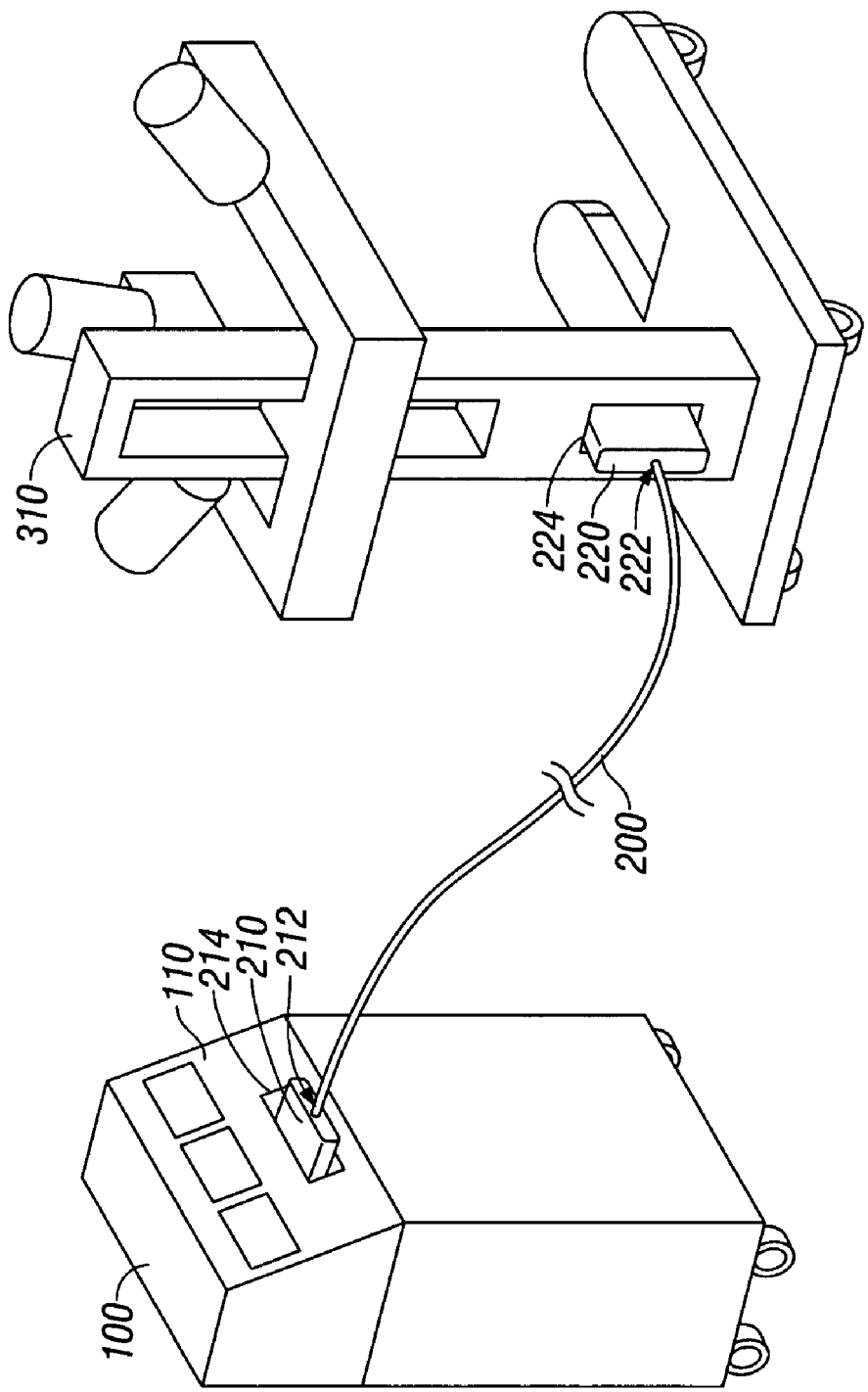
FIG. 1B is a schematic of an electrosurgery generator coupled to a robotic surgery system robotic arm cart according to an embodiment of the present disclosure.

Referring to FIG. 1A, there is disclosed a connection cable 200 having an electrosurgery generator end 212 and a robotic surgical system end 222 for coupling an electrosurgery generator 100 to a robotic surgical system master console 300. Additionally or alternatively, electrosurgery generator 100 can also be coupled by connection cable 200 to a robotic surgical system surgical arm cart 310, as illustrated in FIG. 1B, and/or to other modules (not shown) of the robotic surgical system. Connection cable 200 is detachably coupled at the electrosurgery generator end 212 to electrosurgery generator 100 by connector 210 to a corresponding mating connector 214 provided on electrosurgery generator 100, typically located at, but not limited to, front panel 110 of electrosurgery generator 100.

Connection cable 200 is detachably coupled at robotic surgical system end 222 by connector 220 to a corresponding mating connector 224 provided on at least one of a robotic surgical system master console 300 and located typically on an interface panel 305, a robotic surgical system surgical arm cart 310, or an additional or alternative connector (not shown) provided by the robotic surgical system.

In use, a surgeon or operating room assistant can quickly configure an electrosurgery generator and a robotic surgery system into a robotic electrosurgery arrangement by engaging connector 210 to corresponding mating connector 214 and by engaging connector 220 to its corresponding mating connector 224 or to corresponding mating connector 224 at robotic surgery system surgical arm cart 310, or to a corresponding mating connector (not shown) provided elsewhere at the robotic surgical system.

Figure 2A:
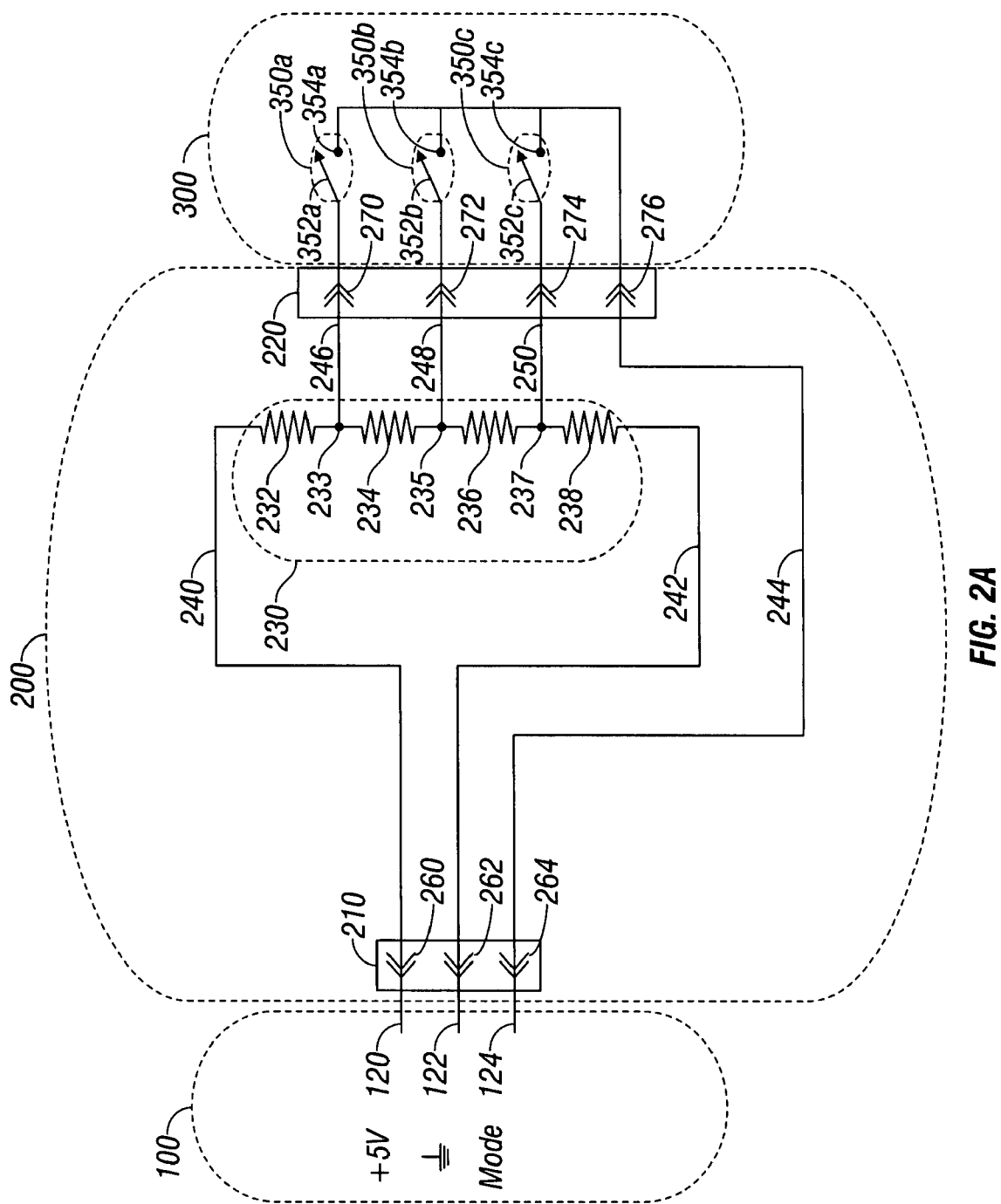
FIG. 2A is a schematic diagram illustrating a connection cable for activating a voltage-controlled electrosurgery generator according to an embodiment of the present disclosure.
Figure 2B:
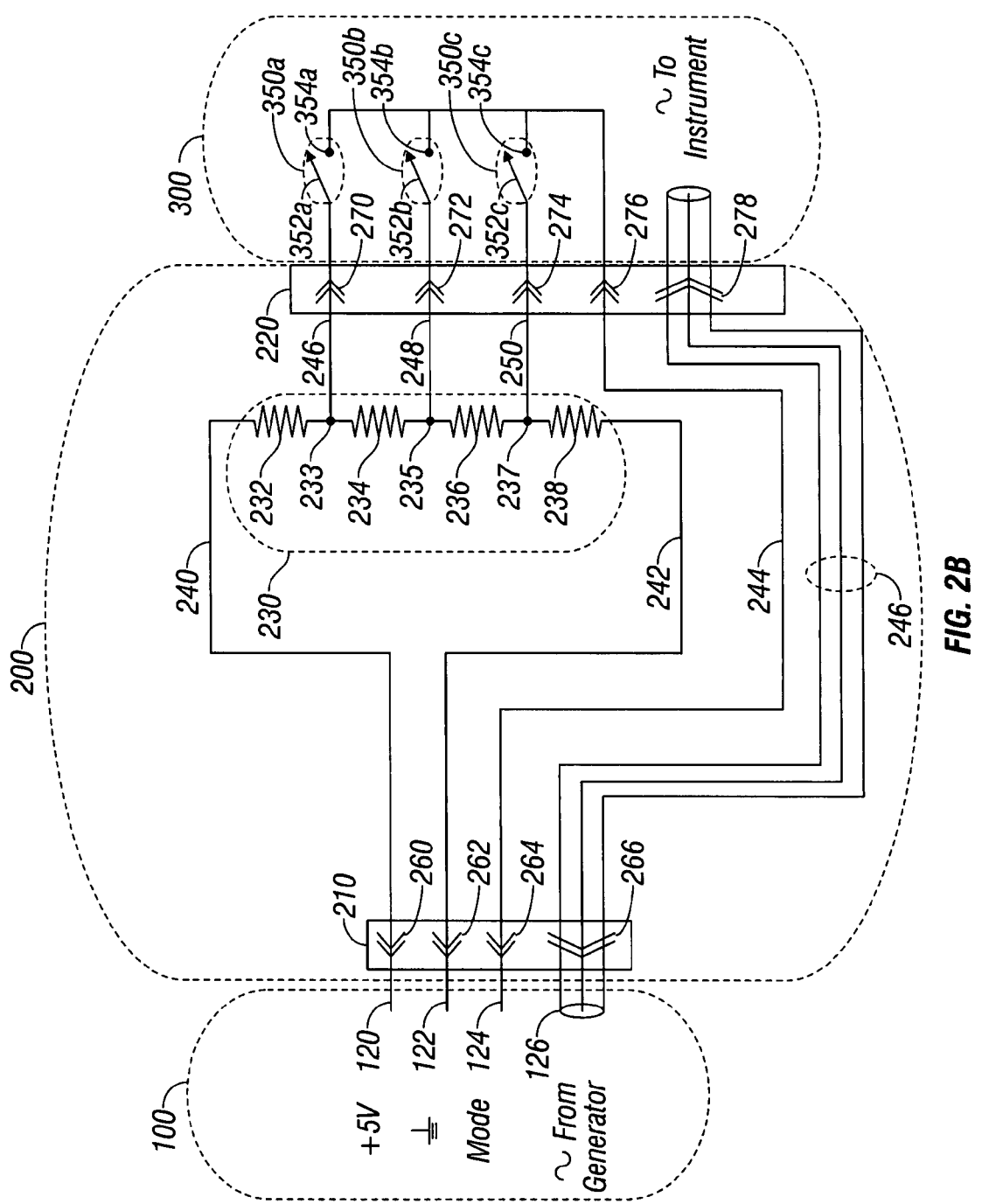
FIG. 2B is a schematic diagram illustrating a connection cable for activating a voltage-controlled electrosurgery generator and for providing an electrosurgical signal to a robotic surgery system according to an embodiment of the present disclosure.

Referring now to FIGS. 2A and 2B, an embodiment of the present disclosure is illustrated wherein electrosurgery generator 100 provides an interface comprising a voltage source 120, a return 122, and a mode input 124. In an embodiment, voltage source 120 provides a substantially constant +5Vdc potential, and return 122 is at ground potential. The electrosurgery generator is configured to generate an electrosurgical signal in response to a control voltage signal applied to mode input 124. As examples only, in response to a +1.67Vdc mode input signal, electrosurgery generator 100 generates a coagulating waveform; in response to a +3.35Vdc mode input a blending waveform is generated; and in response to a +4.18Vdc mode input a cutting waveform is generated. The electrosurgery generator is further configured to determine whether a control voltage input is valid or invalid, to respond only to control voltages recognized as valid, and to ignore all unrecognized (i.e., invalid) voltages. In an embodiment, the electrosurgery generator responds only to mode inputs of +1.67Vdc, +3.35Vdc or +4.18 Vdc; while all other mode input voltages are ignored by the electrosurgery generator. Optionally, mode inputs falling within an accepted tolerance, for example, within +/−0.10 Vdc of any of the nominal voltages known to be valid, are also recognized, thereby causing a corresponding electrosurgical signal to be generated.

Alternate embodiments are envisioned within the present disclosure, such as an electrosurgery generator configured to provide operator-specified waveforms in response to mode inputs, and/or an electrosurgery generator configured to recognize a fewer or greater number of mode input control voltage values and to generate electrosurgery waveforms in accordance thereto.

Further embodiments are envisioned by the present disclosure wherein other aspects of an electrosurgery generator, such as intensity, are controlled. For example, an electrosurgical generator is configured with an "intensity" input adapted to accept an intensity control voltage. A second voltage divider network comprising a plurality of resistors connected in series is provided wherein at each voltage tap a control voltage is made available which represents a control voltage corresponding to a preset intensity setting of the electrosurgical waveform. Alternatively, the additional voltage taps may come from the first voltage divider network. In use, the electrosurgical generator includes an algorithm, library or other data storage device for storing the most recently selected intensity setting for use in connection with the generation of subsequent electrosurgical signals.

At least one control voltage is derived from voltage source 120 and return 122 by voltage divider network 230, which includes a plurality of resistors connected in series. Voltage source 120 and return 122 are operatively and detachably coupled to voltage divider network 230 by connector 210 via conductors 240 and 242, respectively. In an embodiment, voltage divider network 230 comprises resistors 232, 234, 236, and 238 connected in series and intervening voltage taps 233, 235, and 237.

Voltage divider network 230 may be configured such that, in the event that two or more switches are closed simultaneously, an unrecognized control voltage is provided to the mode input of the electrosurgery generator, which is programmed to ignore unrecognized control voltages.

The robotic surgery system may also include one or more switches 350a, 350b and 350c (hereinafter 350a-c) under control of a surgeon operating the robotic surgical system. For the purposes herein the terms "switch" or "switches" includes electrical actuators, mechanical actuators, electro-mechanical actuators (e.g., rotatable actuators, pivotable actuators, toggle-like actuators, buttons, etc.), optical actuators, or other suitable switches. In an embodiment, switches 350a-c are of a normally open, momentary contact, single pole single throw, type having a first contact 352a, 352b, and 352c, respectively (hereinafter 352a-c), and a second contact 354a, 354b, and 354c, respectively (hereinafter 354a-c). Other embodiments are envisioned wherein the switch 350a-c includes a set of relay contacts, a solid state switch, or equivalent switches as may now or hereafter be known in the art. Each first contact 352a-c of switch 350a-c is detachably and operatively coupled by connector 220 to a conductor electrically connected to a corresponding voltage tap, for example, by conductor 246 to voltage tap 233, conductor 248 to voltage tap 235, and conductor 250 to voltage tap 237. Each second contact 354a-c of switch 350a-c is commonly coupled to conductor 244 of connection cable 200, which is detachably and operatively connected to mode input 124 of electrosurgery generator 100 by connector 210.

In use, a surgeon causes the closure of one of the switches 350a-c to complete a circuit, whereby a corresponding control voltage is applied to mode input 124 of electrosurgery generator 100, which, in turn, responds by generating and outputting a corresponding electrosurgery signal.

Figure 3:
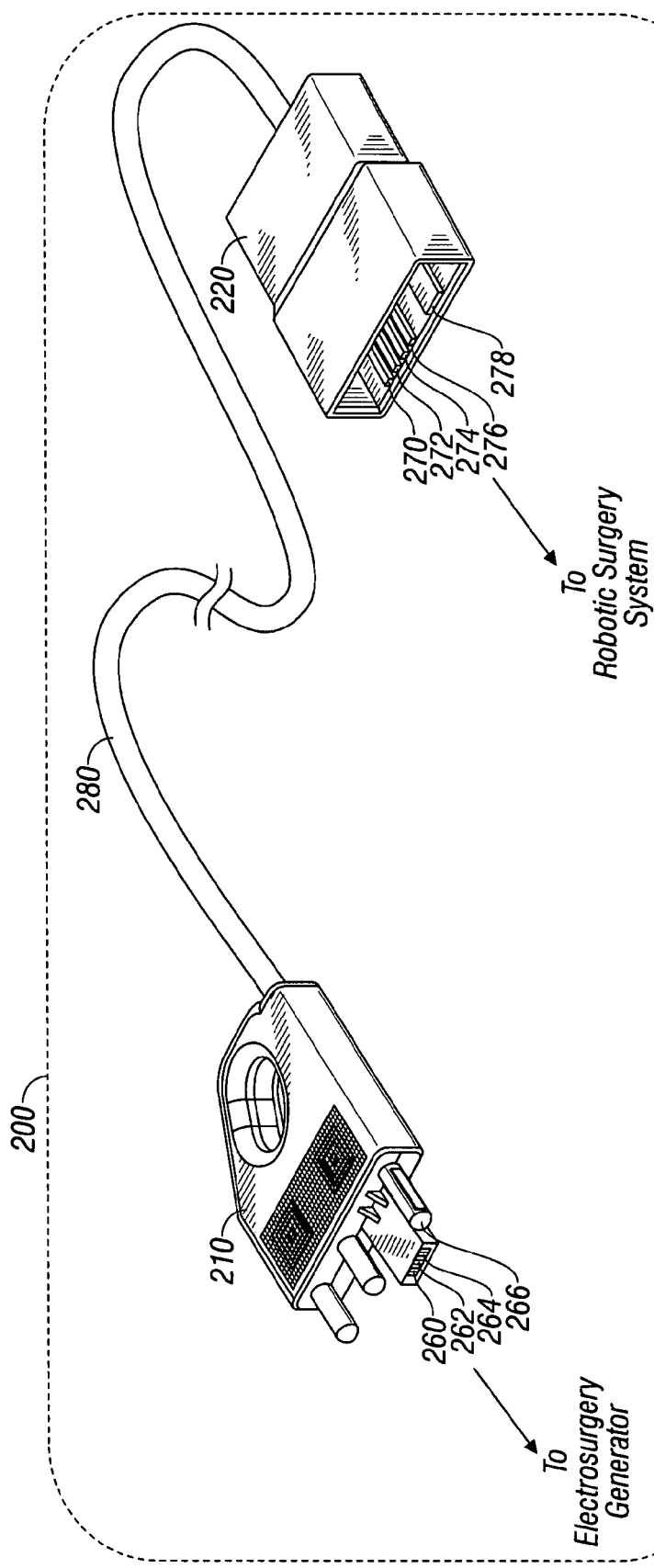
FIG. 3 is a schematic of a connection cable for activating a voltage-controlled electrosurgery generator and for providing an electrosurgical signal to a robotic surgery system in accordance with an embodiment of the present disclosure.

An example embodiment of a connection cable in accordance with the present disclosure is provided with reference to FIG. 3. Connection cable 200 includes a robotic surgery system connector 220 configured to mate with a corresponding connector 224 provided by robotic surgery system as disclosed herein. Cable 280 includes a plurality of independent conductors or wires and electrosurgery generator connector 210 is configured to mate with a corresponding connector 214 provided by a electrosurgery generator as disclosed herein. In an embodiment, cable 280 may be a jacketed cable, a ribbon cable, or other suitable cable.

Robotic surgery system connector 220 may also include contacts 270, 272, and 274 that are disposed in electrical connection with voltage taps 233, 235, and 237, respectively, and contact 276 that is in electrical connection with contact 264 of electrosurgery generator connector 210 via conductor 244. Electrosurgery generator connector 210 may additionally include contacts 260 and 262 that are in electrical connection with voltage divider 230 by conductors 240 and 242, respectively.

Connection cable 200 is optionally configured to deliver the electrosurgical signal from an output 126 of the electrosurgical generator 100 to the robotic surgery system. In an embodiment, electrosurgery generator connector 210 further includes a contact 266, which is in electrical connection via transmission wire 246 of cable 280 to contact 278 of robotic surgery system connector 220.

Variations of the above embodiments are envisioned within the present disclosure. For example, voltage divider 230 may be fully or partially physically supported within connector 210, connector 220, cable 280, or within a separate enclosure independent of (or in combination with) other modules or systems. Further variations of the above-disclosed and other features and functions, or alternatives thereof, may be desirably combined into many other different systems or applications. Various presently unforeseen or unanticipated alternatives, modifications, variations or improvements therein may be subsequently made by those skilled in the art, which are also intended to be encompassed by the following claims.

What is claimed is:

1. A connection cable for activating a voltage-controlled generator, the connection cable comprising:

a first connector adapted to couple to a voltage-controlled generator;

a second connector adapted to couple to a controlling device, the controlling device including at least one circuit element adapted to electrically couple a control voltage to the voltage-controlled generator;

a voltage divider network having a plurality of voltage taps interdisposed between the first connector and the second connector and configured to divide a reference voltage provided by the voltage-controlled generator into at least one control voltage, wherein a control voltage capable of activating the voltage-controlled generator is provided when a single voltage tap is coupled thereto by the controlling device, and a control voltage incapable of activating the voltage-controlled generator is provided when two or more voltage taps are coupled thereto by the controlling device; and a cable including a plurality of electrical wires that couple the first connector, the second connector, and the voltage divider network.

2. The connection cable according to claim 1, wherein the voltage-controlled generator is an electrosurgery generator.

3. The connection cable according to claim 1, wherein the controlling device is a remotely-operated robotic surgery system.

4. The connection cable according to claim 1, wherein the voltage divider network includes a plurality of resistors connected in series.

5. The connection cable according to claim 1, wherein the circuit element includes at least one switch.

6. The connection cable according to claim 5 wherein the at least one switch includes at least one normally open, momentary contact, single-pole single-throw switch.

7. The connection cable according to claim 5, wherein the at least one switch includes at least one normally open, single-pole single-throw relay.

8. The connection cable according to claim 5, wherein the at least one switch includes at least one solid state switch.

9. A method for activating a voltage-controlled generator from a controlling device, the method comprising the steps of:

providing a voltage-controlled generator and a controlling device;

providing a connection cable comprising:

a first connector adapted to couple to the voltage-controlled generator;

a second connector adapted to couple to the controlling device, the controlling device including at least one circuit element adapted to electrically couple a control voltage to the voltage-controlled generator;

a voltage divider network having a plurality of voltage taps interdisposed between the first connector and the second connector and configured to divide a reference voltage provided by the voltage-controlled generator into at least one control voltage, wherein a control voltage capable of activating the voltage-controlled generator is provided when a single voltage tap is coupled thereto by the controlling device, and a control voltage incapable of activating the voltage-controlled generator is provided when two or more voltage taps are coupled thereto by the controlling device; and a cable including a plurality of electrical wires that couple the first connector, the second connector, and the voltage divider network;

operably coupling the voltage-controlled generator and a controlling device with the connection cable;

in the connection cable, dividing the reference voltage provided by the voltage-controlled generator into at least one control voltage;

at the connection cable, receiving at least one control signal originating within the controlling device;

selecting a control voltage in accordance with the received control signal;

determining whether the control voltage is valid;

activating the voltage-controlled generator in response to a determination that the received control voltage is valid; and inhibiting the activation of the voltage-controlled generator in response to determination that the received control signal is not valid.

10. The method according to claim 9, further comprising the step of transmitting the signal to a destination device.

11. The method according to claim 10, wherein the destination device is a surgical instrument.

12. The method according to claim 9, wherein the voltage-controlled generator is an electrosurgery generator.

13. The method according to claim 9, wherein the controlling device is a robotic surgery system.

14. The method according to claim 9, wherein the resultant signal is an electrosurgery signal.

* * * * *